(12) United States Patent
Berry

(10) Patent No.: US 10,869,660 B2
(45) Date of Patent: Dec. 22, 2020

(54) MALLEABLE RETRACTOR FOR SPINAL SURGERY

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 140 days.

(21) Appl. No.: 16/265,752

(22) Filed: Feb. 1, 2019

(65) Prior Publication Data

US 2020/0245856 A1  Aug. 6, 2020

(51) Int. Cl.
- *A61B 1/32* (2006.01)
- *A61B 17/02* (2006.01)
- *A61B 17/00* (2006.01)

(52) U.S. Cl.
CPC ............ *A61B 17/0293* (2013.01); *A61B 1/32* (2013.01); *A61B 2017/00946* (2013.01); *A61B 2017/0225* (2013.01); *A61B 2017/0256* (2013.01)

(58) Field of Classification Search
CPC ............................. A61B 1/32; A61B 17/0293
See application file for complete search history.

(56) References Cited

U.S. PATENT DOCUMENTS

| | | | | |
|---|---|---|---|---|
| 380,745 | A * | 4/1888 | Chamberlin | A61B 1/32 600/224 |
| 2,053,868 | A * | 9/1936 | Grosso | A61B 17/0293 600/233 |
| 5,509,893 | A * | 4/1996 | Pracas | A61B 1/32 600/184 |
| 2005/0149035 | A1 * | 7/2005 | Pimenta | A61B 17/02 606/86 R |
| 2005/0215863 | A1 * | 9/2005 | Ravikumar | A61B 17/3423 600/204 |

* cited by examiner

*Primary Examiner* — Christian A Sevilla
(74) *Attorney, Agent, or Firm* — Ellenoff Grossman & Schole LLP; James M. Smedley; Alex Korona

(57) ABSTRACT

The present invention generally relates to a retractor. Specifically, this invention relates to a malleable retractor designed to retract soft tissue and create a surgical opening to provide visualization of and access to the spine.

11 Claims, 7 Drawing Sheets

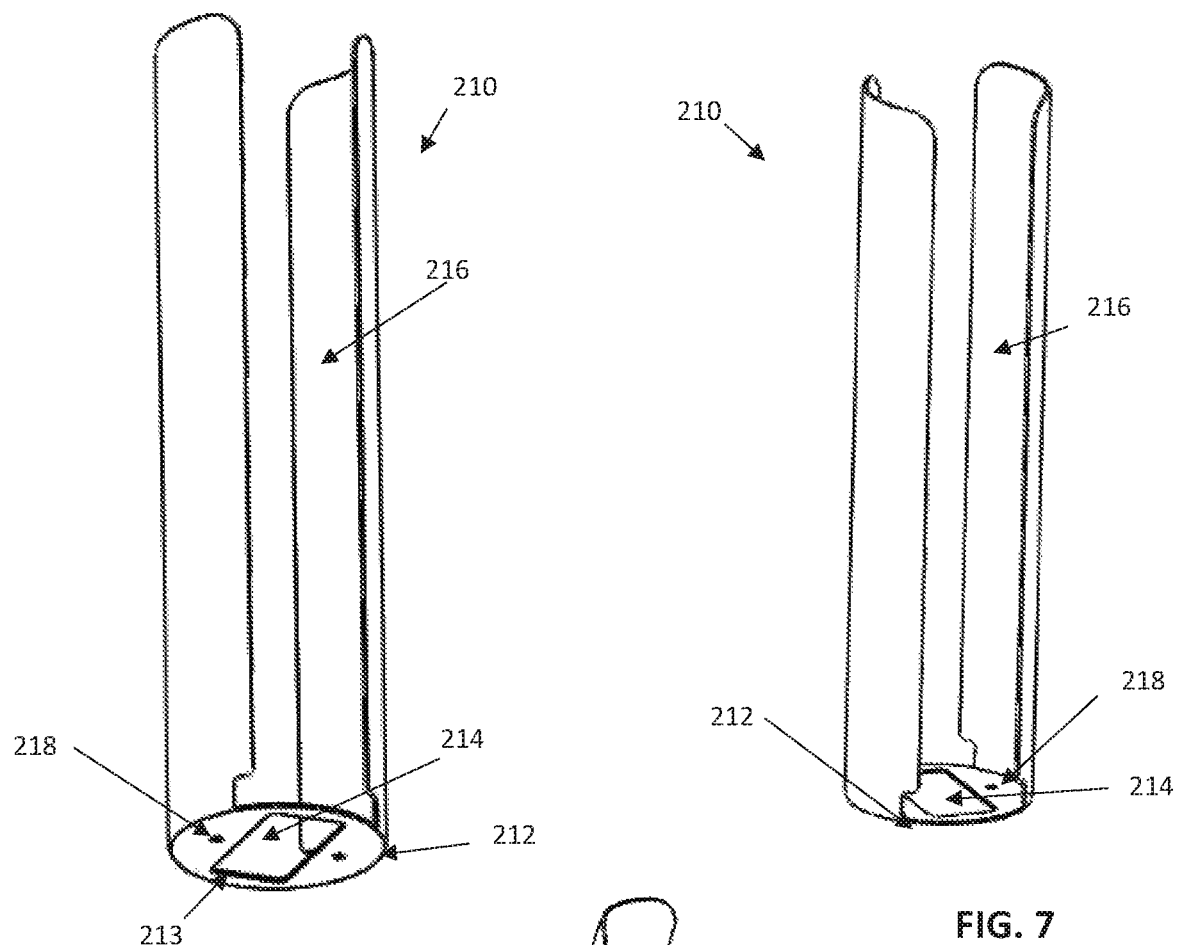
FIG. 6
FIG. 7
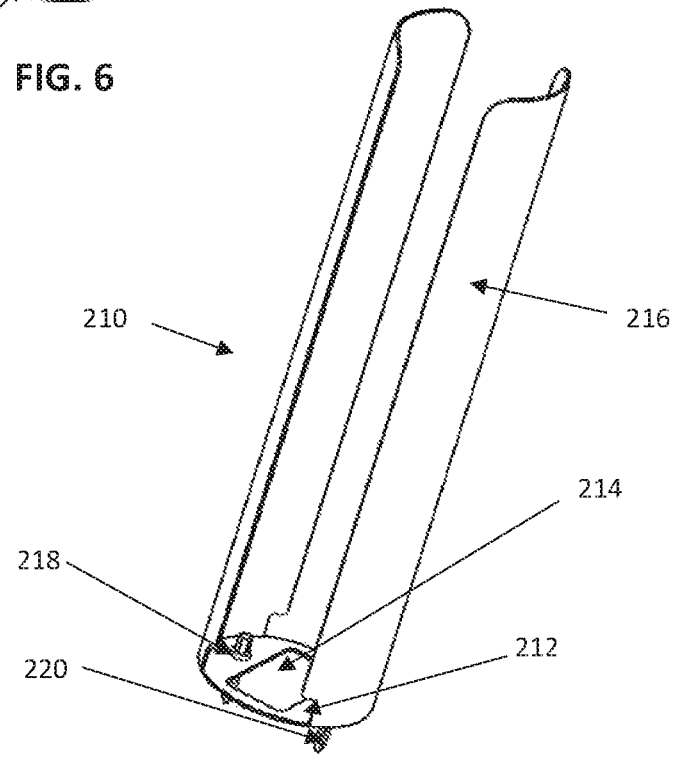
FIG. 8

MALLEABLE RETRACTOR FOR SPINAL SURGERY

FIELD OF THE INVENTION

The present invention generally relates to a retractor device. Specifically, this invention relates to a malleable retractor device designed to retract soft tissue and create a surgical opening to provide visualization of and access to the spine.

BACKGROUND OF THE INVENTION

Minimally invasive surgical approaches have been developed and applied to orthopedic surgeries such as spinal fusions. For example, conditions such as scoliosis may be corrected by releasing or cutting contractures of the disc annulus during lateral and inter-body fusions. Spinal operations involving lateral and anterior inter-body fusions have significant advantages over other approaches to the lumbar in that they allow the placement of large inter-body fusion cages, minimizing subsidence during operation.

Currently available retractors for inter-body fusions typically use rigid blade configurations which are constructed to be fixated to a ring or base located exterior to a surgical cavity. Other retractor systems rely on rigid blades or arms, attached to a base or ring, similarly located exterior to the surgical cavity. Additionally, some of the presently available retractors incorporate pins or screws to anchor the blades to the spine. The anchor members utilized by these retractors are generally long, having a length extending from the exterior portion of the surgical cavity to the vertebrae, necessitating the use of a bulky device for use along both the interior and exterior portions of the surgical cavity. These apparatuses obstruct the operating surgeon's view as well as the surgeon's ability to place instruments and implants into the surgical site. Additionally, due to the fixed, small superficial surgical cavities facilitated during spinal operations, the angle at which an instrument can be inserted into a surgical cavity is restricted and, because the blades are rigid and affixed to a base section or ring outside of the surgical cavity, the internal aperture which the surgeon must work through is similarly restricted. Although the blades may be able to expand to create a larger working area at the external end of the surgical cavity, the internal opening is generally fixed. Furthermore, there is little advantage to a larger aperture at the external end, since the targeted interbody space is limited.

Another retractor device currently available is made of thin, flexible metal. This version of the device has blades hinged to a base at its bottom and allows perpendicular blades to both swing away from each other, as well as flex open in a circumferential manner. While this creates a larger exterior surgical cavity which is advantageous for placing multiple pedicle screws, it is not necessarily advantageous for interbody work. The device maintains a narrow opening at its base which restricts the size and number of instruments which can be utilized by an operating surgeon and restricts broad visualization by the surgeon. Although this version of the device does not have the bulk of the previously available devices, it is still limited in its application as it restricts the angle at which an instrument can be inserted into the surgical cavity. Furthermore, this version of the device does not have any means with which to anchor to the spine, thereby allowing it to freely move within the soft tissue.

Therefore, there is a need in the art for a malleable retractor that is configured to allow a base to be placed within a surgical cavity, against the spine, and manipulatable blades to create enhanced access and visualization. These and other features and advantages of the present invention will be explained and will become obvious to one skilled in the art through the summary of the invention that follows.

SUMMARY OF THE INVENTION

Accordingly, embodiments of the present invention are directed to a retractor device comprised of a base, an aperture and blades. Embodiments of the present invention may include a base and blades that are malleable, allowing for surgical access to vertebrae by the retraction soft tissue.

According to an embodiment of the present invention, a retractor device for increasing a surgeon's visualization and working area during surgery is provided, the retractor device comprising: a base, an aperture and a plurality of blades.

According to an embodiment of the present invention, a retractor device comprising a base section and two or more blades extending from the base section, wherein each of the blades has a first end attached to an outer edge of the base section and a second end that is opposite the first end.

According to an embodiment of the present invention, the retractor device further comprises an aperture formed in the base section, wherein the aperture is defined by an inner edge of the base section.

According to an embodiment of the present invention, the retractor device further comprises one or more anchor ports formed in the base section.

According to an embodiment of the present invention, the one or more anchor ports are configured to engage with anchor members.

According to an embodiment of the present invention, the anchor ports are positioned between an inner edge of the base section and the outer edge of the base section.

According to an embodiment of the present invention, each of the blades of the retractor device has a curved shape.

According to an embodiment of the present invention, the base section of the retractor device has circular shape and the curved shape of each of the blades corresponds to the circular shape of the base section.

According to an embodiment of the present invention, the second end of each of the blades of the retractor device is configured to splay outward to expand a visualization and workable area.

According to an embodiment of the present invention, the first end of each of the blades is attached to the base section of the retractor device by a hinge.

According to an embodiment of the present invention, the hinge of the blades is formed of a flexible material.

According to an embodiment of the present invention, a retractor device comprising a base section; an aperture formed in the base section, wherein the aperture is defined by an inner edge of the base section; and two or more blades extending from the base section, wherein each of the blades has a first end attached to an outer edge of the base section and a second end that is opposite the first end.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

FIG. 6 shows a bottom elevational view of the retractor device in accordance with an embodiment of the present invention.

FIG. 7 shows a top elevational view of the retractor device in accordance with an embodiment of the present invention.

FIG. 8 shows a top elevational view of the retractor device with anchor ports and anchor members in accordance with an embodiment of the present invention.

DETAILED SPECIFICATION

Figure 1:
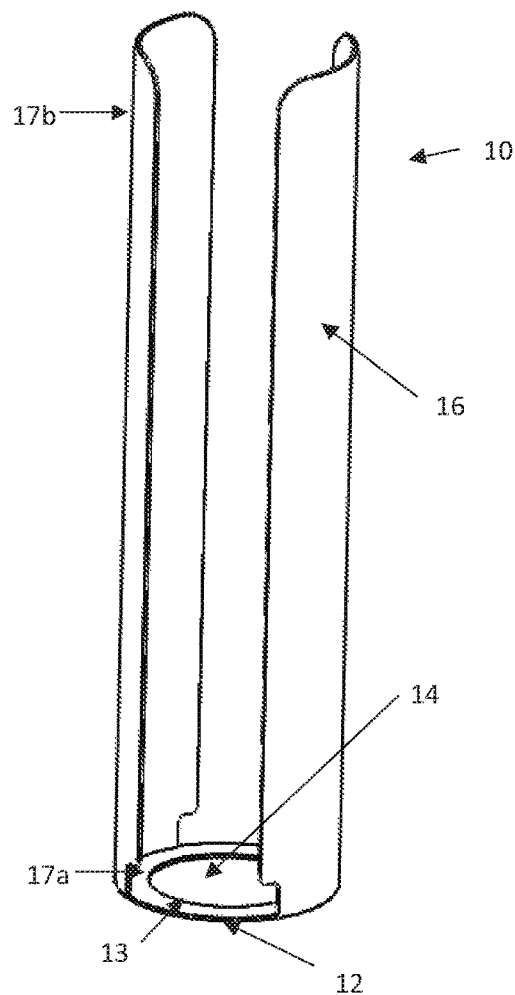
FIG. 1 shows a top elevational view of a retractor device with perpendicular blades in accordance with an embodiment of the present invention.

The present invention generally relates to a retractor device. Specifically, this invention relates to a malleable retractor designed to retract soft tissue and to provide access to the spine during various surgical operations.

The proposed retractor blade is designed for use during surgical procedures, to create surgical exposure to the spine and the interbody space. Importantly, the disclosed device provides augmented exposure to a surgical site, offering surgeons access to and enhanced visualization of the spine. Furthermore, a retractor device in accordance with embodiments of the present invention may be anchored to the spine to maintain its placement along a vertebrae of interest.

Generally, during an operation on the spine, a surgeon creates a surgical cavity by forming an incision or wound in a patient body. According to embodiments of the present invention, a surgeon may place the retractor device in accordance with an embodiment of the present invention into the body cavity over a K-wire. Once the K-wire is in the surgeon's chosen position, a sequential dilation apparatus, such as a tube, may be inserted over the K-wire to dilate the surgical cavity to a desired degree in order to install the retractor device. The surgeon may then remove the sequential dilation apparatus and manipulate the retractor device into its desired shape and orientation.

According to embodiments of the present invention, a retractor device is comprised of a base section formed with an aperture and blades that extend from the base section. Additional components may include anchor ports in the base section and anchor members that secure the base section to a desired vertebra. Some embodiments of the present invention may include fewer or additional components depending on the specific application of the retractor. One of ordinary skill in the art would appreciate that there are many possible configurations and components for a retractor, and embodiments of the present invention are contemplated for use with any such configuration or component. In some embodiments, the entire device is made from malleable metal. This allows the device to be bent and flexed into the desired position and orientation, while still being sturdy enough to retract the soft tissue as necessary.

According to embodiments of the present invention, the blades of the retractor may be constructed of a variety of malleable materials. In some embodiments, the blades may be constructed of a resilient material. In a preferred embodiment, at least a portion of the blades may be comprised of any variety of malleable materials having the ability to hold their shape after being bent into a desired position and suitable for use inside the human body. One of ordinary skill in the art would appreciate that there are numerous suitable materials the blades of the retractor could be manufactured, and embodiments of the present invention are contemplated for use with any such material.

According to embodiments of the present invention, the retractor device comprises two or more blades with each blade having a first and second end. In some embodiments, the blades are attached to the base of the retractor at their first end. In some embodiments, the blades are substantially flat. In some embodiments, the blades are substantially curved. In some embodiments, curved blades give the retractor a substantially round or substantially circular cross-section. In some embodiments, the blades are substantially linear at their first and second ends. In some embodiments, the blades are constructed to extend past the exterior of a surgical cavity once the retractor is fully implanted at the desired surgical location. In some embodiments, the blades are bent at their second end to facilitate a surgeon in expanding the surgical cavity opening to allow for enhanced visualization of the desired vertebrae at the site of the surgical cavity.

According to embodiments of the present invention, the blades of the retractor device may be coupled to the base of the retractor by hinges. In some embodiments, the hinges connecting the blades to the base are flexible. In some embodiments, the hinges are formed of a resilient material.

According to an embodiment of the present invention, the retractor comprises a base section. In a preferred embodiment, the base section is formed with an aperture and blades extending therefrom. In the preferred embodiment, the aperture is defined by an inner edge of the base section. The aperture may provide a surgeon with visualization and surgical access to a desired portion of the spine. In the preferred embodiment, the blades extend from the outer edge of the based section. In some embodiments, the blades may be splayed to provide a surgeon with access to the spine through the aperture. In some embodiments, the base section may include anchor ports. In some embodiments, anchor members engage with the anchor ports to fasten the retractor device to a chosen vertebra. In some embodiments, a threaded portion of the anchor members engage with a threaded portion of the anchor ports to fasten the retractor device to the chosen vertebra.

Referring generally now to FIGS. 1-15, a retractor device in accordance with embodiments of the present invention is shown.

Figure 2:
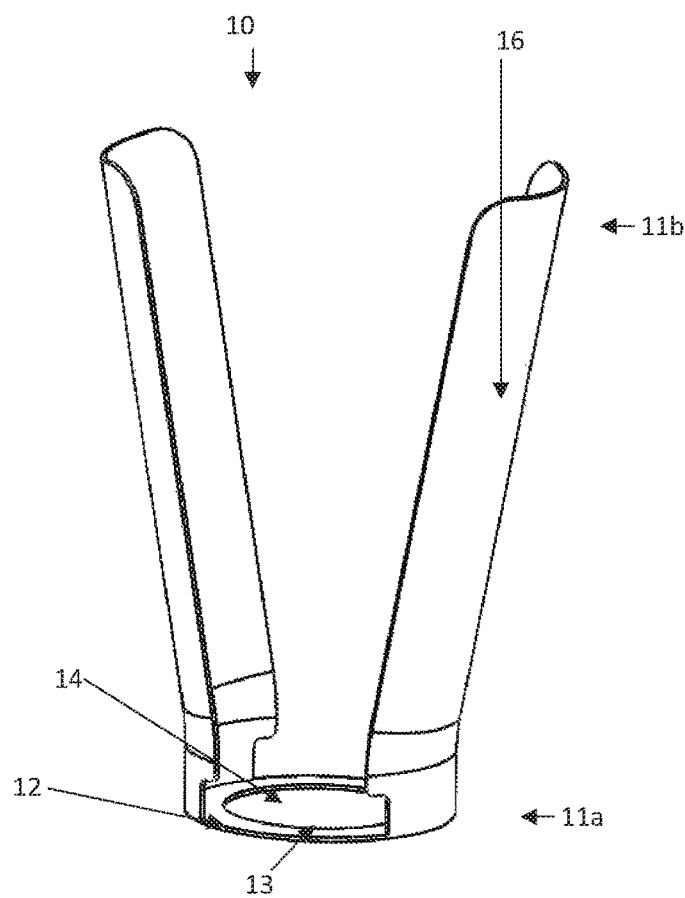
FIG. 2 shows a top elevational view of a retractor device with splayed blades in accordance with an embodiment of the present invention.
Figure 3:
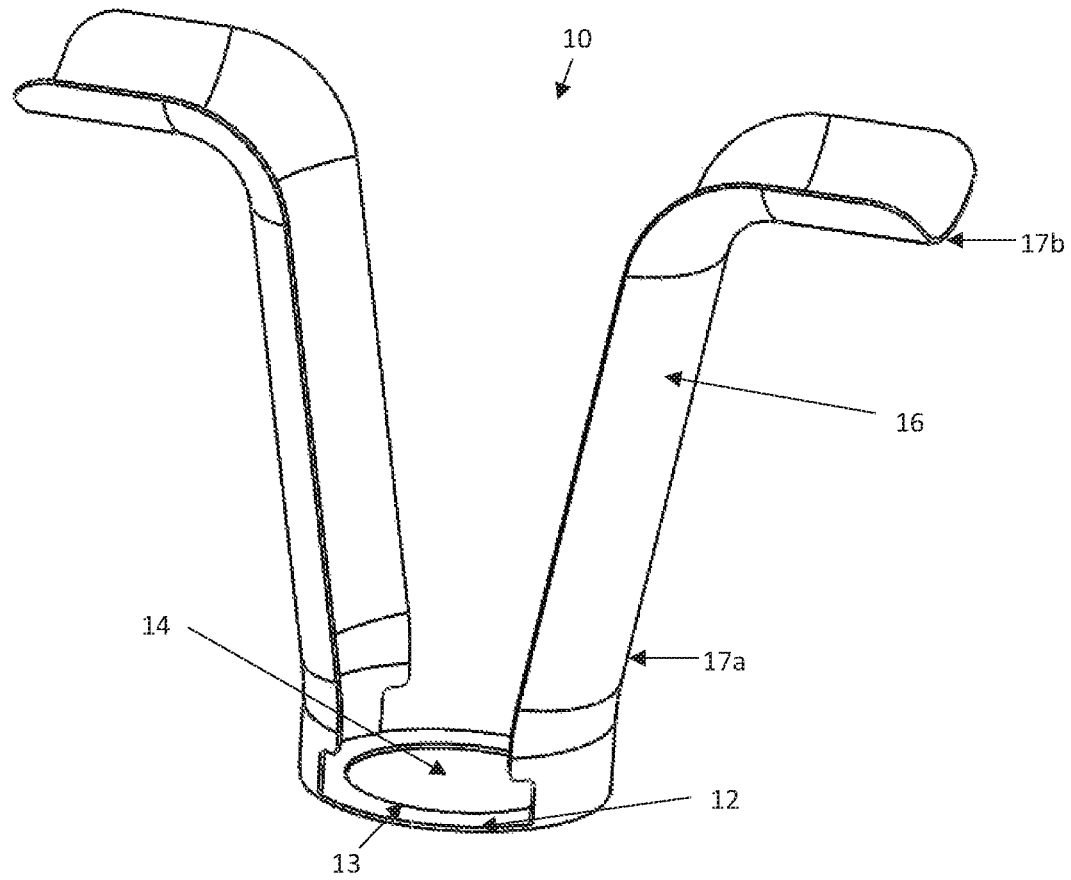
FIG. 3 shows a top-side elevational view of the retractor device with splayed and bent blades in accordance with an embodiment of the present invention.

FIGS. 1-3 show a retractor device in accordance with an embodiment of the present invention. As shown in FIG. 1, in some embodiments, the retractor 10 of the present invention has a base section 12 and an aperture 14 defined by the inner edge 13 of the base section 12. Extending from the base 12 are a plurality of blades 16 having a first end 17a and a second end 17b. In some embodiments, the blades 16 may be made from a malleable material which is capable of holding its shape after it has been bent into a desired position. As further shown in FIG. 1, the blades 16 are in their insertion position when the blades are oriented perpendicular to the base 12. In some embodiments, the blades 16 are rounded as to create a tube-like effect, which allows the retractor 10 to be inserted into a dilation tube.

As shown in FIG. 2, the blades 16 of retractor 10 may be splayed outward to expand the second end 11b of the retractor 10. In this embodiment, the base 12 and aperture 14 are maintained and do not expand at the first end 11a of the retractor 10.

As shown in FIG. 3, the blades 16 may be bent at their second end 17b. A surgeon may fold a portion of blades 16 which have not been inserted into the surgical cavity, such that the surgeon's view of the surgical field is not obstructed by the portion of blades 16 which have not been inserted into the surgical cavity.

Figure 4:
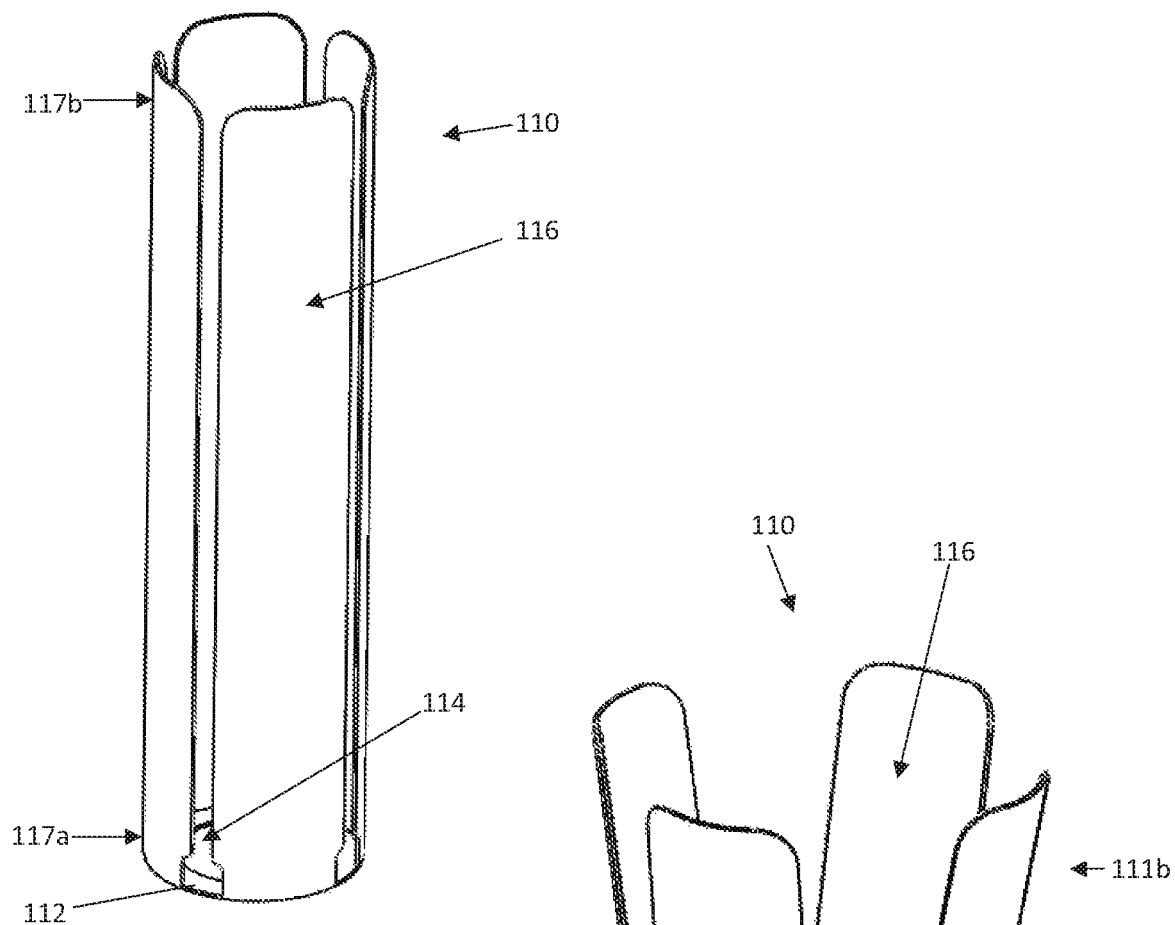
FIG. 4 shows a top-side elevational view of the retractor device in accordance with an embodiment of the present invention.
Figure 5:
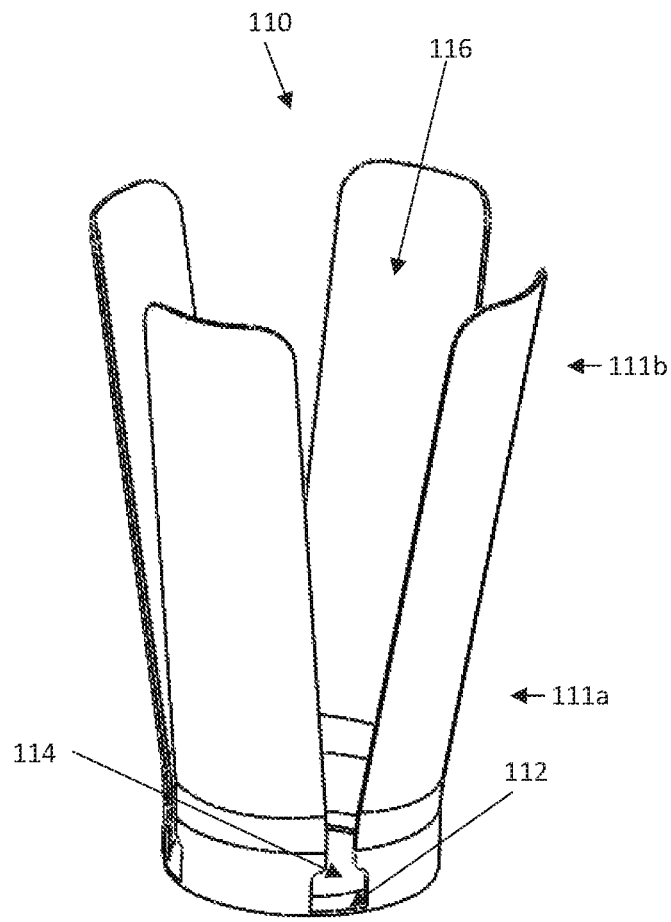
FIG. 5 shows a top-side elevational view of the retractor device with splayed blades in accordance with an embodiment of the present invention.

FIGS. 4-5 show a retractor device in accordance with an embodiment of the present invention. As shown in FIG. 4, the retractor 110 has a base section 112 with an aperture 114. Extending from the base 112 are a plurality of blades 116 having a first end 117a and a second end 117b. In some embodiments, the blades 116 may be made from a malleable material which is capable of holding its shape after it has been bent into a desired position. As further shown in FIG. 4, the blades 116 are in their insertion position when the blades are oriented perpendicular to the base 112. In some embodiments, the blades 116 are rounded as to create a tube-like effect, which allows the retractor 110 to be inserted into a dilation tube.

As shown in FIG. 5, the blades 116 may be splayed outward to expand the second end 11b. In this embodiment, the base 112 and aperture 114 are maintained and do not expand at the first end 111a FIGS. 6-15 show a retractor device in accordance with an embodiment of the present invention. As shown in FIG. 6, the retractor has a base section 212, an aperture 214 defined by the inner edge 213 of the base section 212, and at least one anchor port 218. Extending from the base 212 are a plurality of blades 216. Blades 216 may be made from malleable material which is capable of holding its shape after it has been bent into a desired position. As shown in FIGS. 6-7, the retractor 210 is in its insertion position when the blades 216 are oriented perpendicular to the base 212. Furthermore, the blades 216 may be rounded as to create a tube-like effect, which allows the retractor 210 to be inserted into a dilation tube.

As shown in FIG. 8, the retractor 210 is in its insertion position wherein blades 16 are perpendicular to the base 212. In some embodiments, base 212 may be comprised of anchor ports 218 allowing for the insertion of anchor members 220 therethrough.

Figure 9:
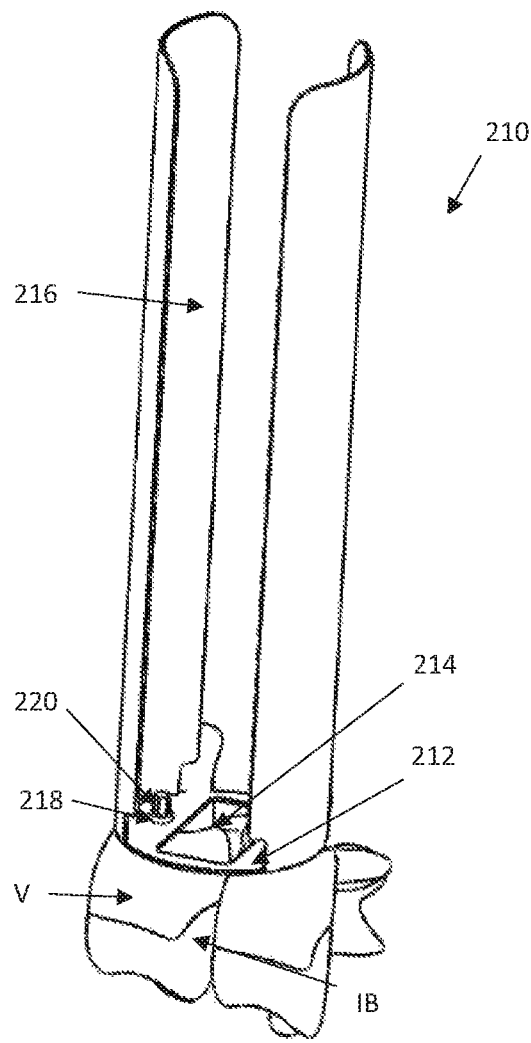
FIG. 9 shows a top-side elevational view of the retractor with anchor ports and anchor members attached to a spine in accordance with an embodiment of the present invention.
Figure 10:
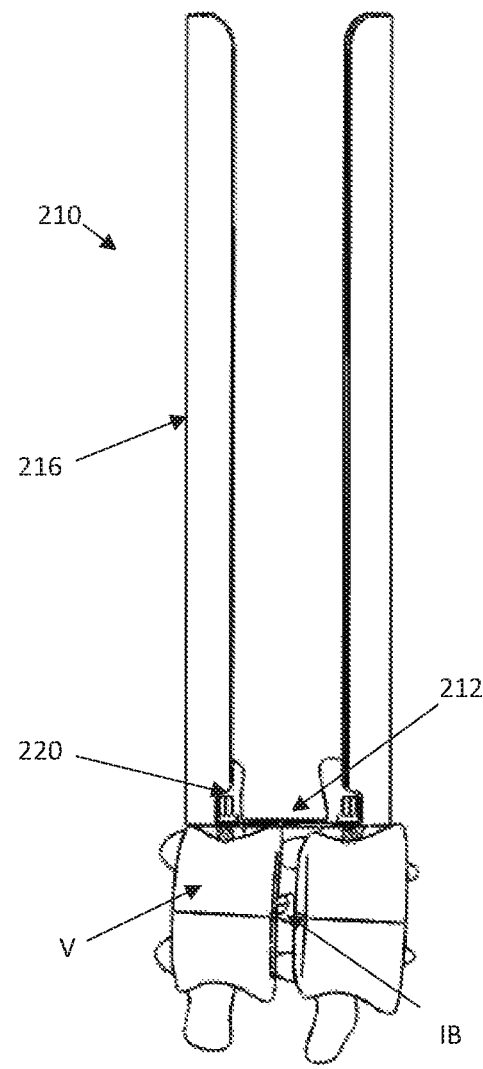
FIG. 10 shows a side view of the retractor device with anchor ports and anchor members attached to a spine in accordance with an embodiment of the present invention.
Figure 11:
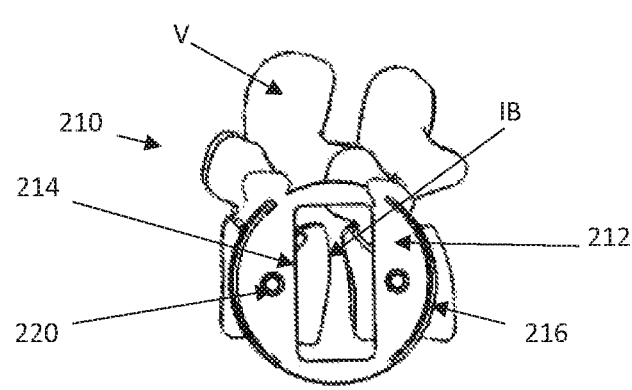
FIG. 11 shows a top view of the retractor device with anchor ports and anchor members attached to a spine in accordance with an embodiment of the present invention.

As shown in FIGS. 9-11, the retractor 210 may be inserted and anchored into a vertebrae V. Anchor members 220 may be placed through anchor port 218 located on the base 212 and into the vertebrae V. Anchor members 220 are constructed to hold the retractor 210 in its desired place. Anchor members 220 assist in providing access to interbody space IB through the aperture 214.

Figure 12:
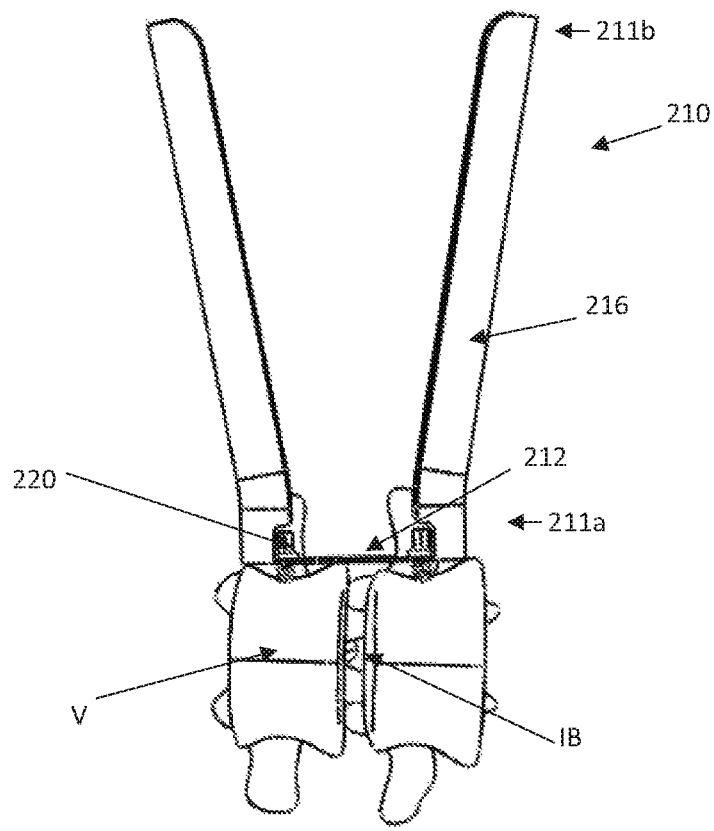
FIG. 12 shows a side view of the retractor device with splayed blades and anchor ports and anchor members attached to a spine in accordance with an embodiment of the present invention.
Figure 13:
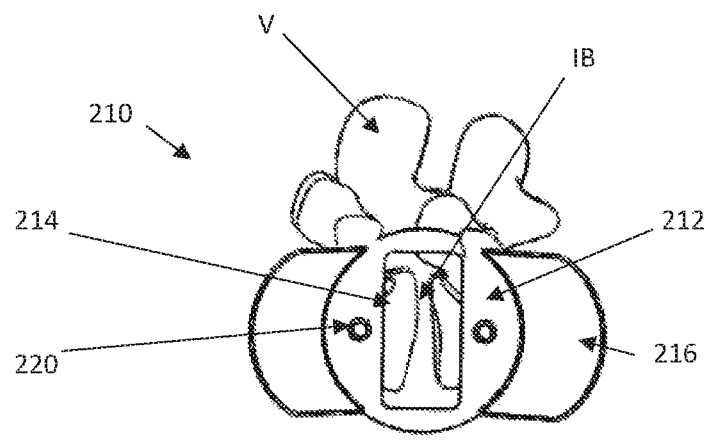
FIG. 13 shows a top view of the retractor device with splayed blades and anchor ports and anchor members attached to a spine in accordance with an embodiment of the present invention.

As shown in FIGS. 12-13, the blades 216 may be splayed outward to expand the second end 211b. In this embodiment, the base 212 and aperture 214 are maintained and do not expand at the first end 211a. Furthermore, the retractor 210 is maintains its location along vertebrae V by the anchor members 220. The surgeon's visualization and access through the aperture 214 to the interbody space IB is maintained even though the blades 216 may be in their deformed or manipulated state.

Figure 14:
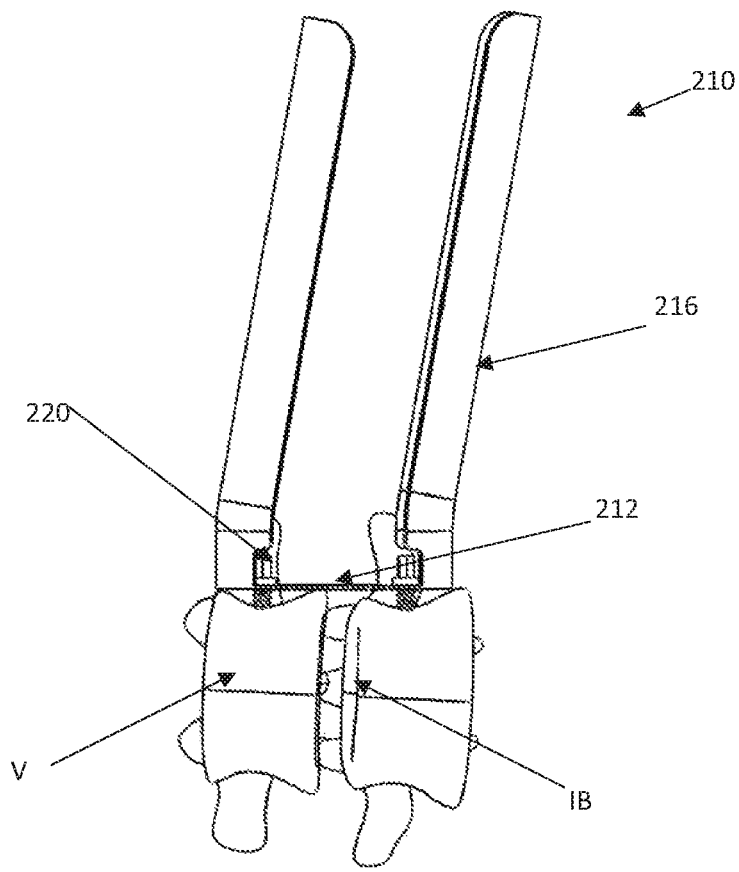
FIG. 14 shows a side view of the retractor device with a splayed blade and anchor ports and anchor members attached to the spine in accordance with an embodiment of the present invention.
Figure 15:
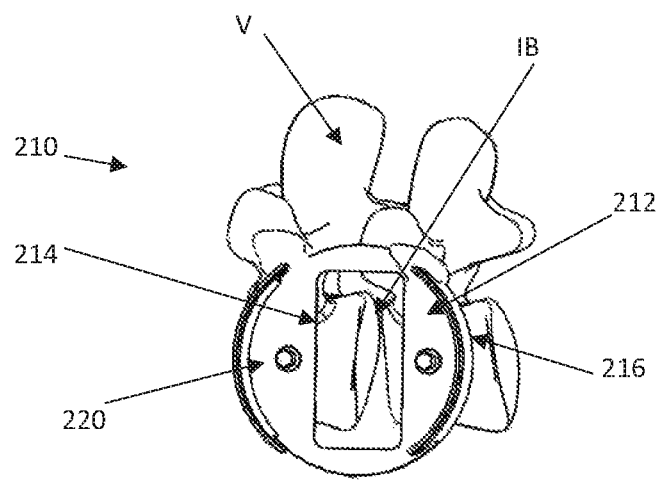
FIG. 15 is a top view of the retractor device with anchor ports and anchor members attached to the spine in accordance with an embodiment of the present invention.

As shown in FIGS. 14-15, one of the blades 216 is splayed outward to expand the second end 211b opening, while the opposite blade is splayed inward. This might need to be done in order to avoid other bony structures, such as the iliac crest or the rib cage. In this embodiment, the base 212 and aperture 214 are maintained and do not expand at the first end 211a. Furthermore, the retractor 210 maintains its location along vertebrae V via the anchor ports 218 that engage with the anchor members 220 that are secured in the vertebrae V. The surgeon's visualization and access through the aperture 214 to the interbody space IB is maintained even though the blades 216 may be in their deformed or manipulated state.

The terminology used herein is for the purpose of describing particular embodiments only and is not intended to be limiting of the invention. As used herein, the term "and/or" includes any and all combinations of one of more of the associated listed items. It will further be understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. A retractor device comprising:
    a base section;
    two or more blades extending from said base section, wherein each of said blades has a first end attached to an outer edge of said base section and a second end that is opposite said first end;
    one or more anchor ports formed in said base section;
    wherein said one or more anchor ports are positioned between an inner edge of said base section and said outer edge of said base section;

wherein each of said blades has a curved shape; and wherein said base section has circular shape and said curved shape of each of said blades corresponds to said circular share of said base section.

2. The retractor device of claim 1, further comprising an aperture formed in said base section, wherein said aperture is defined by an inner edge of said base section.

3. The retractor device of claim 1, wherein said one or more anchor ports are configured to engage with anchor members.

4. The retractor device of claim 1, wherein said second end of each of said blades is configured to splay outward to expand a visualization and workable area.

5. The retractor device of claim 1, wherein said first end of each of said blades is attached to said base section by a hinge.

6. The retractor of claim 5, wherein said hinge is formed of a flexible material.

7. A retractor device comprising:

a base section;

an aperture formed in said base section, wherein said aperture is defined by an inner edge of said base section;

two or more blades extending from said base section, wherein each of said blades has a first end attached to an outer edge of said base section and a second end that is opposite said first end;

one or more anchor ports formed in said base section;

wherein said one or more anchor ports are positioned between said inner edge of said base section and said outer edge of said base section;

wherein each of said blades has a curved shape; and wherein said base section has circular shape and said curved shape of each of said blades corresponds to said circular shape of said base section.

8. The retractor device of claim 7, wherein said one or more anchor ports are configured to engage with anchor members.

9. The retractor device of claim 7, wherein said second end of each of said blades is configured to splay outward to expand a visualization and workable area.

10. The retractor device of claim 7, wherein said blades are attached to said base section by hinges.

11. The retractor of claim 10, wherein said hinges are formed of a flexible material.

\* \* \* \* \*